United States Patent [19]
Davies

[11] Patent Number: 5,840,586
[45] Date of Patent: *Nov. 24, 1998

[54] METHOD AND APPARATUS FOR ANTENATAL RISK ASSESSMENT FOR CHROMOSOMAL ABNORMALITIES FACTORING IN MATERNAL AGE INFLUENCE

[75] Inventor: Christopher John Davies, Energlyn Park, United Kingdom

[73] Assignee: Clinical Diagnostic Systems, Inc., Rochester, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 565,498

[22] Filed: Nov. 30, 1995

Related U.S. Application Data

[63] Continuation of Ser. No. 275,180, Jul. 14, 1994, abandoned.

[30] Foreign Application Priority Data

Jul. 22, 1993 [GB] United Kingdom ............... 9315230

[51] Int. Cl.$^6$ ................... G01N 33/53; G01N 33/92
[52] U.S. Cl. ................. 436/510; 436/65; 436/71; 436/131; 436/518; 436/811; 436/817; 705/2
[58] Field of Search ................ 436/65, 86, 87, 436/131, 510, 518, 811, 817, 818, 71; 364/413.09; 705/2

[56] References Cited

U.S. PATENT DOCUMENTS

| | | | |
|---|---|---|---|
| 4,454,232 | 6/1984 | Breglio et al. | 436/504 |
| 4,874,693 | 10/1989 | Bogart | 435/7 |
| 5,252,489 | 10/1993 | Macri | 436/87 |
| 5,258,907 | 11/1993 | Marci | 364/413.01 |
| 5,506,150 | 4/1996 | Canick et al. | 436/510 |

FOREIGN PATENT DOCUMENTS

| | | |
|---|---|---|
| 0327337 | 8/1989 | European Pat. Off. . |
| WO-A-94 12884 | of 0000 | WIPO . |
| A-89-0696 | 1/1989 | WIPO . |
| A-90-08325 | 7/1990 | WIPO . |

OTHER PUBLICATIONS

Spencer et al, Ann Clin Biochem, 29, 506–518, 1992.
Wald et al., Brit. J. Obst. Gyn., 95, 334–341 (1988).
Wald et al., Brit. Med. J., 297, 883–887, (1988).
Reynolds et al., Ann. Clin. Biochem., 27, 452–458 (1989).

*Primary Examiner*—David Saunders

[57] ABSTRACT

The present invention provides a more accurate risk assessment of antenatal screening results because the maternal age of the patient is considered in evaluating the results from various common screening markers, and especially the results from UE determinations.

3 Claims, 12 Drawing Sheets

METHOD AND APPARATUS FOR ANTENATAL RISK ASSESSMENT FOR CHROMOSOMAL ABNORMALITIES FACTORING IN MATERNAL AGE INFLUENCE

This is a continuation of application Ser. No. 08/275,180, filed Jul. 14, 1994 and now abandoned, which is hereby incorporated by reference.

FIELD OF THE INVENTION

This invention relates to a method for antenatal screening for chromosomal abnormalities and to an apparatus for performing the method. In particular, it relates to a method and apparatus for antenatal screening for Down Syndrome.

BACKGROUND OF THE INVENTION

The risk of Down Syndrome and some other chromosomal abnormalities in an unborn child is known to increase with the age of the mother and it is this knowledge which forms the basis for selection of pregnant women for further investigation. Further investigation for instance in the case of Down Syndrome involves sampling of the amniotic fluid by amniocentesis, a procedure which itself carries a risk for the mother, induction of a miscarriage being a recognized hazard of this procedure.

Maternal serum and other markers for Down Syndrome are widely used for antenatal screening for this chromosomal abnormality, the most common of these markers being alpha-fetoprotein (AFP), human chorionic gonadotropin (hCG)—either the intact molecule thereof or its beta subunit—and unconjugated estriol (UE). Disclosures relating to the use of these markers in antenatal screening for Down Syndrome include U.S. Pat. No. 4,874,693, WO 89/00696 and WO 90/08325.

Maternal serum screening is based on selecting a subgroup of women who are at the greatest risk of giving birth to a child with an abnormality, in whom the risks of an invasive diagnostic procedure are considered to be outweighed by the risk of the abnormality. The risk is calculated by multiplying the age related risk by the likelihood ratio. The likelihood ratio is calculated from the relative frequencies of the multivariate Gaussian distribution functions of marker analytes in affected and unaffected pregnancies, corresponding to the value of the individual serum marker concentrations.

Since the concentrations of the various analytes vary with gestational age, the analyte concentrations must be normalized. This is performed by dividing the concentration of the analyte by the median concentration expected for that particular gestational age in women with unaffected pregnancies. This is termed the multiple of the median (MoM).

The use of two or more markers together in antenatal screening can be advantageous. For example the markers AFP, hCG and UE can be used together. The combination of marker analytes gives significantly more information than is given by any single marker alone, or by the group of markers when used sequentially. The use of likelihood ratios derived from a multivariate combination is an efficient means of deriving information relating to a woman's risk of carrying an affected child.

Hitherto it has generally been assumed that information relating to a woman's risk of carrying an unaffected child which is derived from markers such as AFP, hCG and UE is independent of maternal age. We believe that this assumption is correct with AFP and hCG and in many other instances. However in some instances, and particularly with UE, the assumption is not correct and the information relating to risk is influenced by maternal age. Therefore when using markers such as UE, allowance should be made for maternal age when processing any information which is obtained.

SUMMARY OF THE INVENTION

According to the present invention we provide a method for antenatal screening for one or more predetermined chromosomal abnormalities comprising:

measuring one or more barkers, precursors or metabolites of the markers in a body fluid sample of a pregnant patient, comparing the measured level of the one or more markers, precursors or metabolites of the markers and the gestational age of the fetus of the patient to reference values of the one or more markers, precursors or metabolites of the markers at various gestational ages, whereby allowance in the comparing is made for the maternal age of the patient, the reference values being obtained from (a) pregnant women carrying fetuses having the one or more predetermined abnormalities, and from (b) pregnant women carrying normal fetuses, and the comparison being indicative of the risk of the patient carrying a fetus with the one or more predetermined chromosomal abnormalities.

This invention also provides an apparatus comprising:

means adapted for receiving measurements of one or more markers or precursors or metabolites of the markers useful for antenatal screening for one or more chromosomal abnormalities in a body fluid sample of a pregnant patient, and computer means for comparing the measurements to sets of reference data obtained from (a) pregnant women carrying fetuses having the one or more predetermined chromosomal abnormalities, and from (b) pregnant women carrying normal fetuses, the computer means also adjusting the level of the markers or precursors or metabolites of the markers for the maternal age of the patient.

The present invention provides a more accurate risk assessment of antenatal screening results because the maternal age of the patient is considered in evaluating the results from various common screening markers, and especially the results from UE determinations.

DETAILED DESCRIPTION OF THE INVENTION

Figure 1:
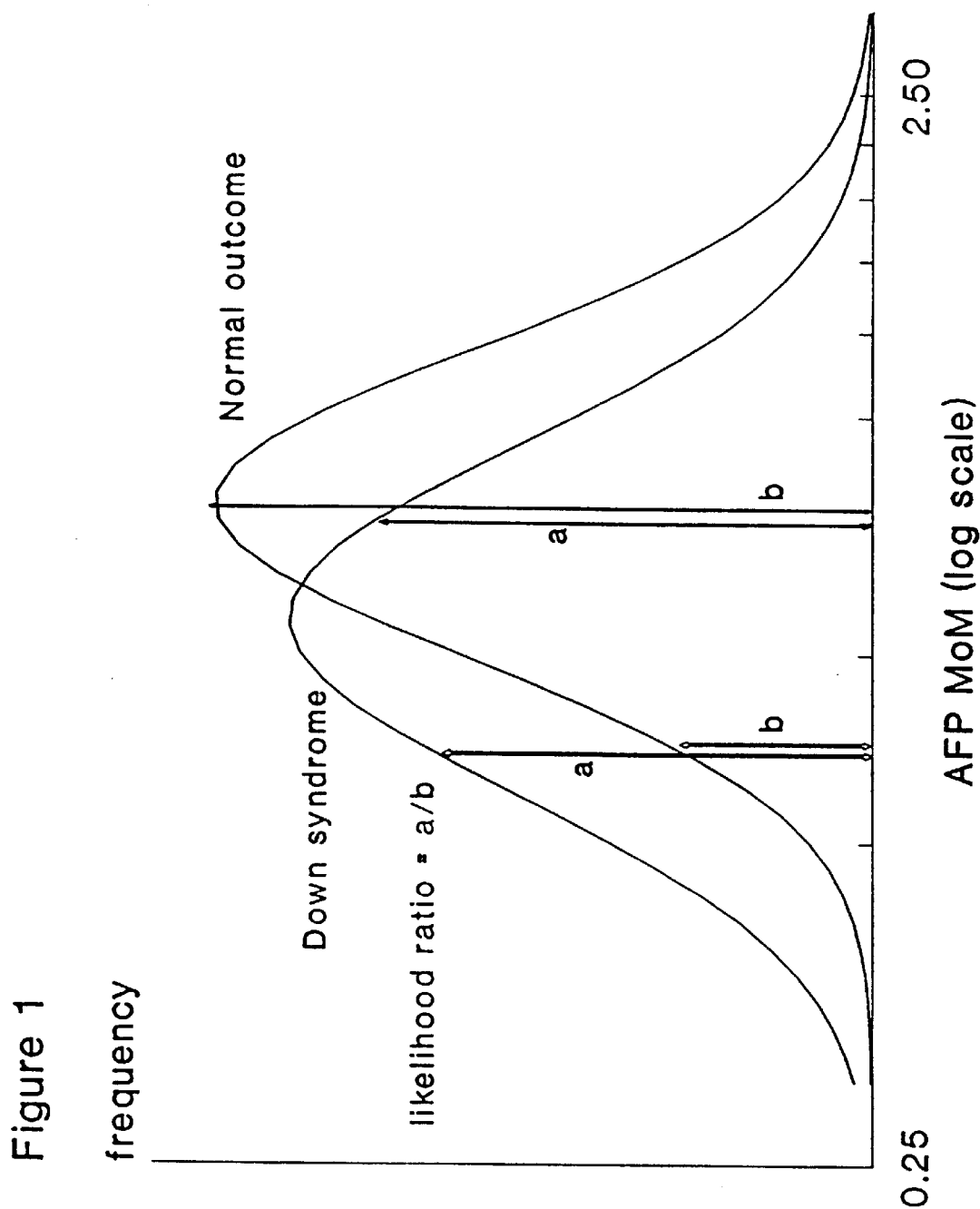
FIG. 1 is a diagram of frequency against AFP MoM (log scale)

The maternal body fluids on which measurements are made include, for example, saliva, urine, amniotic fluid and particularly blood. Preferably the marker is a serum or plasma marker.

The method of the invention can be used for antenatal screening for a wide range of chromosomal abnormalities. The most significant and frequently occurring of these is Down Syndrome (Trisomy 21). Other abnormalities which may be screened by using the invention include Edwards Syndrome (Trisomy 18), Pateaus Syndrome (Trisomy 13), Turner Syndrome, Monosomy X and Kleinefelter Syndrome. The method of the invention may be used to screen for individual abnormalities or to screen for groups of abnormalities together. For example, it could be used to screen for both Down Syndrome and Edwards Syndrome.

Markers whose levels in a women's blood are affected by age include dehydroepiandrosterone sulfate (DHEAS), 16-alpha-hydroxy-dehydroepiandrosterone sulfate (16-alpha-hydroxy DHEAS) and, particularly UE and precursors or metabolites of these.

The method of the invention can be used to analyze risk using other serum markers in blood samples in combination with the age-affected marker. Such other markers include alpha-fetoprotein (AFP), inhibin (In), progesterone (Pr), human chorionic gonadotropin (hCG)—either the intact molecular or its beta subunit, pregnancy associated plasma protein A (PAPPA), and precursors and metabolites of these markers and UE, DHEAS and 16-alpha-hydroxy-DHEAS if not already included. Thus, one or more of these other markers may be measured together with the principal markers to be measured by the method of the invention. For example, the method of the invention may be used with hCG, PAPPA and UE as the markers to be measured.

Measurements are carried out and analyzed using the method of the invention on blood samples taken during an appropriate period of pregnancy. Preferably the measurements are made on blood samples taken in the first trimester and especially in the period between the beginning of the eighth week and the end of the thirteenth week of gestation (8th to 13th weeks). The woman's measured serum value for the individual serum marker is divided by the expected median value found in women with unaffected pregnancies at the same gestational age, to derive the MoM. The probability that the MoM values for the combination of serum markers tested belongs to the multivariate distribution of values found in unaffected pregnancies is calculated. The same calculation is performed by reference to the probability that the individual combination of values forms part of the multivariate distribution found in abnormal pregnancies. The ratio of the two probabilities is termed the likelihood ratio (LR) which indicates the likelihood that an individual woman has an affected pregnancy or not. The degree of separation between the multivariate distributions for affected and unaffected pregnancies changes with gestational age, i.e. there is a continuous change in the manner of calculating probability depending upon the gestational age. This continuous change can be built into the algorithm used in the calculation.

An individual woman has an age related risk which is independent of the maternal serum marker concentrations. The woman's age related risk, by Baye's theorum, is modified by multiplying by the likelihood ratio (LR) obtained previously to derive a combined risk. This combined risk may then be used to counsel the woman regarding the relative risk of the abnormality as opposed to the risk of miscarriage associated with a subsequent diagnostic invasive procedure.

Figure 2:
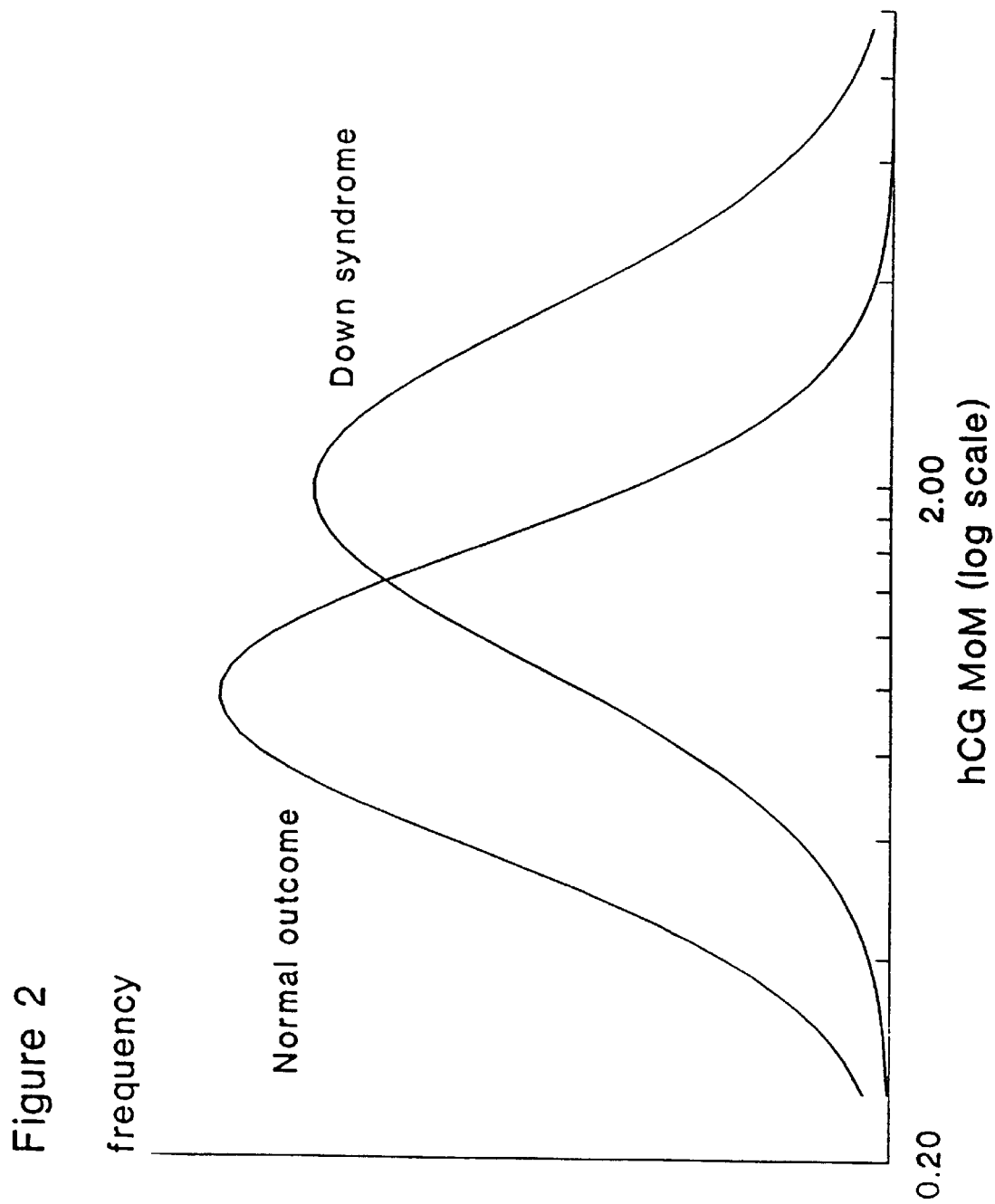
FIG. 2 is a diagram of frequency against hCG MoM (log scale)
Figure 3:
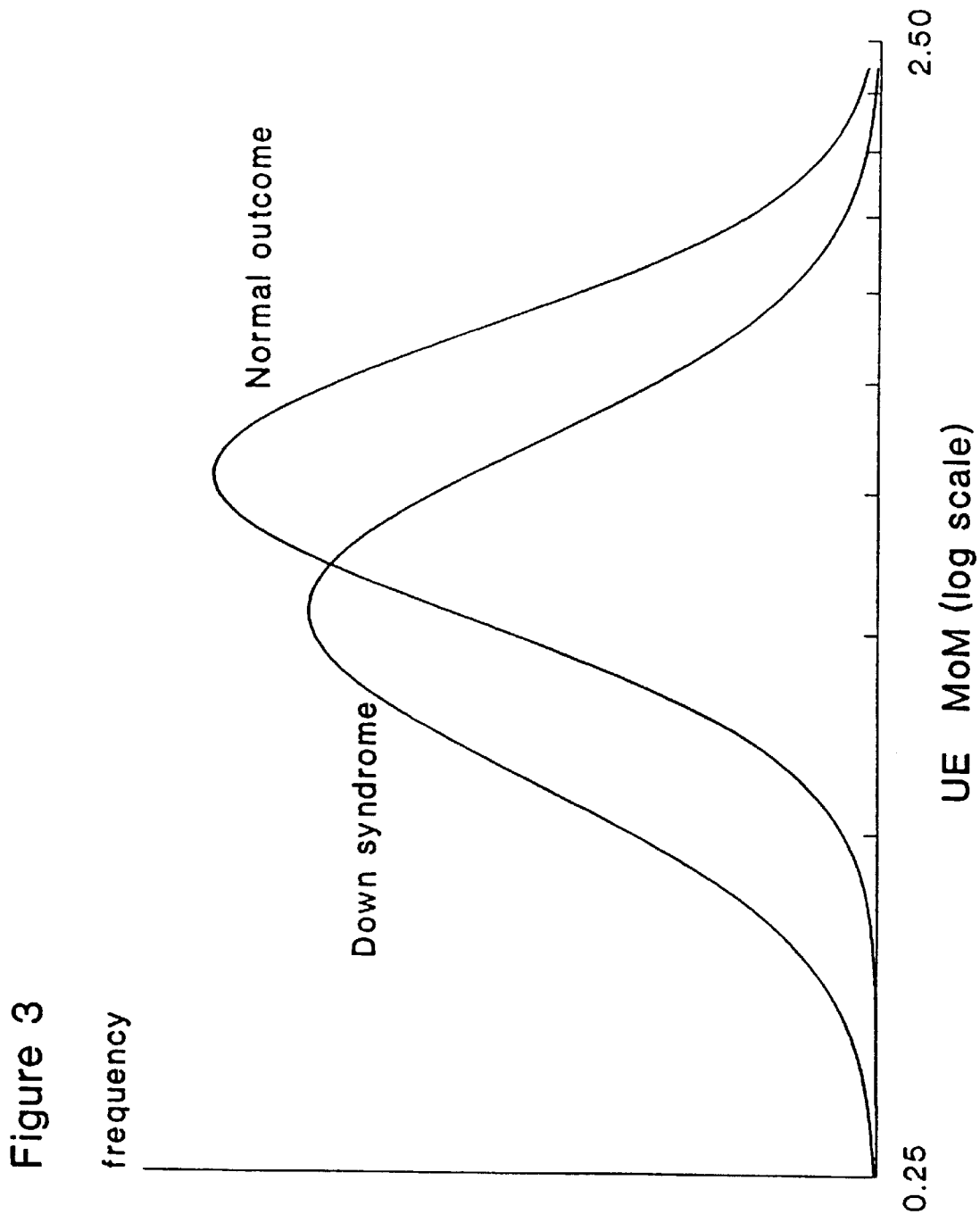
FIG. 3 is a diagram of frequency against UE MoM (log scale)

FIG. 1 demonstrates the principles involved in calculating the likelihood that a sample came from a Down Syndrome affected pregnancy, in this case for maternal serum alpha-fetoprotein (AFP), although the same principle applies to human chorionic gonadotropin (hCG), unconjugated estriol (UE) or indeed any marker, biochemical or otherwise in which the distributions in affected and unaffected pregnancies differ. The distributions in affected and unaffected pregnancies for hCG an UE are shown in FIGS. 2 and 3 respectively.

The invention is further illustrated by the following examples:

EXAMPLE 1

The Relationship Between Maternal Age and Maternal Serum Unconjugated Estriol

Two large databases were examined for a relationship between maternal serum concentrations of biochemical markers and maternal age. The first (Trials A) was a set of 2545 women with normal outcome pregnancies. The data came from 5 sites throughout Europe. The second set of data (Trials B) consisted of 3124 women from a single laboratory in the United Kingdom who were being screened for neural tube defects. All samples were assayed for maternal serum alpha-fetoprotein (AFP); human chorionic gonadotropin (hCG), and unconjugated estriol (UE), using KODAK AMERLEX-M second trimester assays according to the manufacturers' (Kodak Clinical Diagnostics Ltd., Amersham, UK) instructions. Both KODAK and AMERLEX are Trademarks. For each trial, center medium values were established at each week of normal gestation from 15 to 20 completed weeks of pregnancy. A regression equation was calculated for each analyte relating the median analyte value to the numbers of days of gestation. AFP and UE showed a logarithmic increase with gestational age, whereas hCG showed an exponential decline over the weeks studied. Separate regressions were established for each study center.

Each sample result was then converted to the multiple of the median value by dividing by the expected median found at that gestational age.

Figure 4:
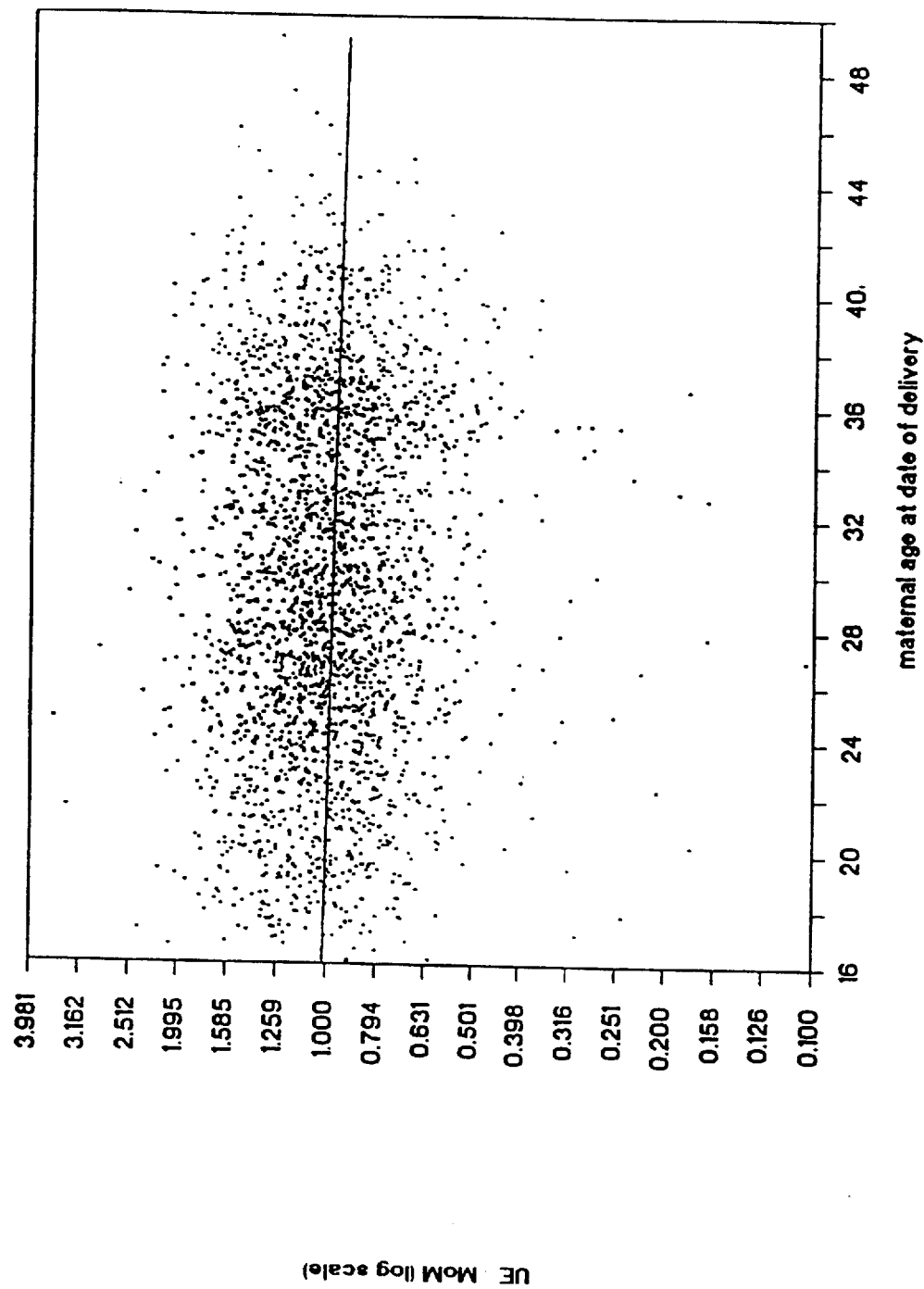
FIG. 4 is a plot of UE MoM (log scale) against maternal age at date of delivery for data from Trials A in Example 1.
Figure 5:
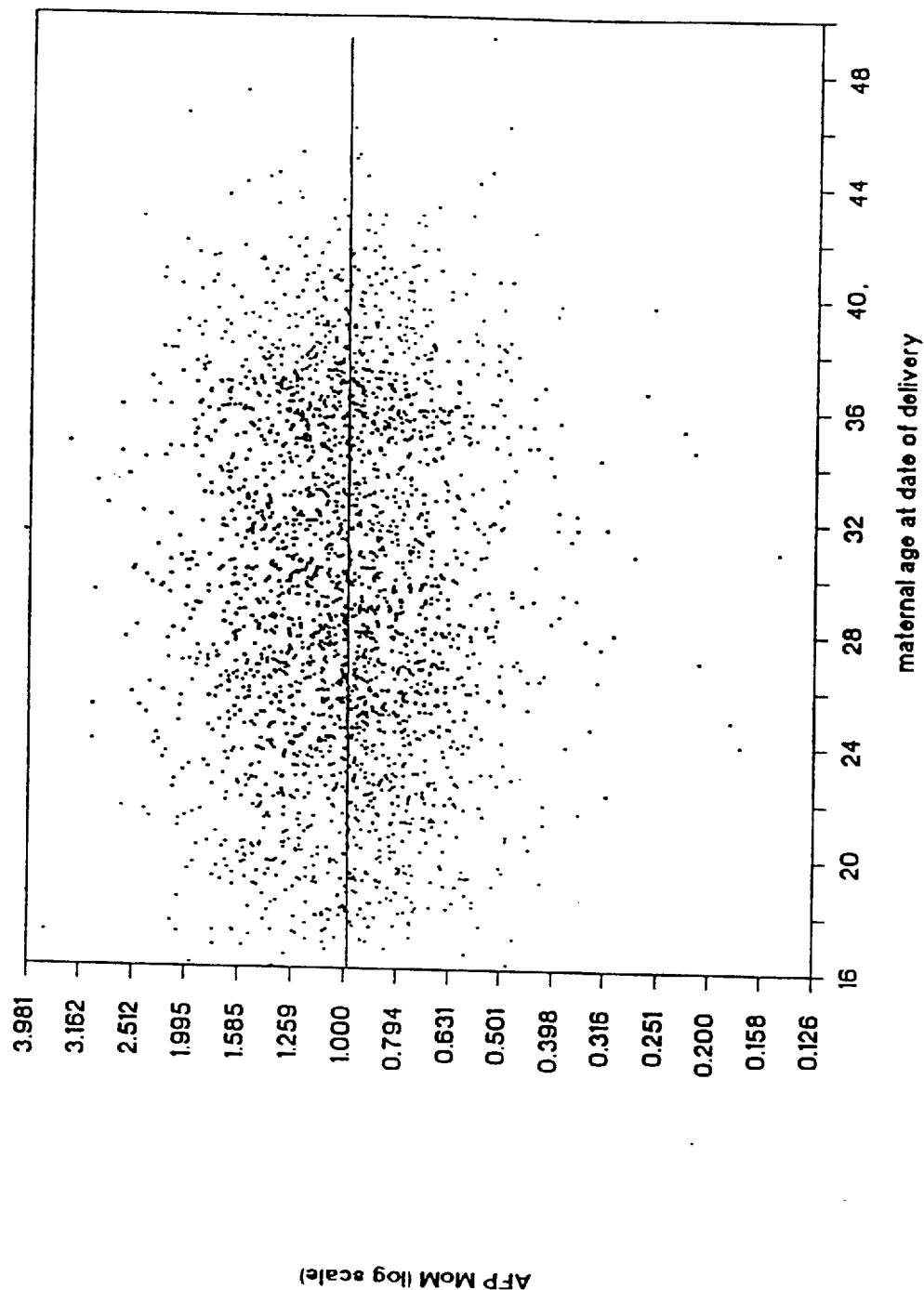
FIG. 5 is a plot of AFP MoM (log scale) against maternal age at date of delivery for data from Trials A in Example 1.
Figure 6:
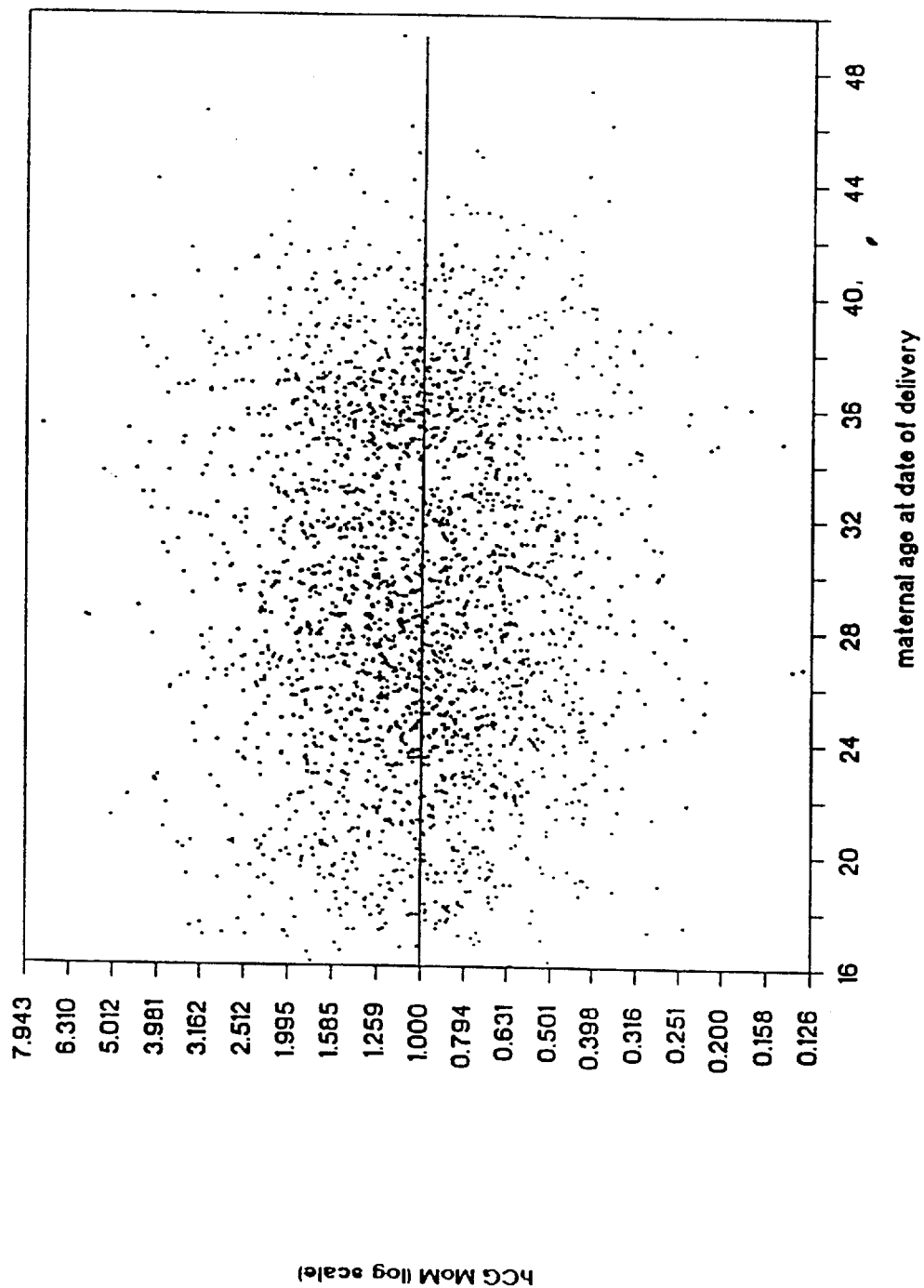
FIG. 6 is a plot of hCG MoM (log scale) against maternal age at date of delivery for data from Trials A in Example 1.

FIG. 4 shows the relationship between unconjugated estriol and maternal age at the expected date of delivery for data from Trials A. There is a highly statistically significant relationship with unconjugated estriol being lower in older women than in younger. The relationship was best described by regression of the natural log of the MoM value against maternal age at the expected date of delivery, as all three analytes (AFP, hCG, UE) were found to follow a log Gaussian distribution. No relationship was found in these women between maternal age and either maternal serum AFP MoM or maternal serum hCG MoM (FIGS. 5 and 6 respectively).

Figure 7:
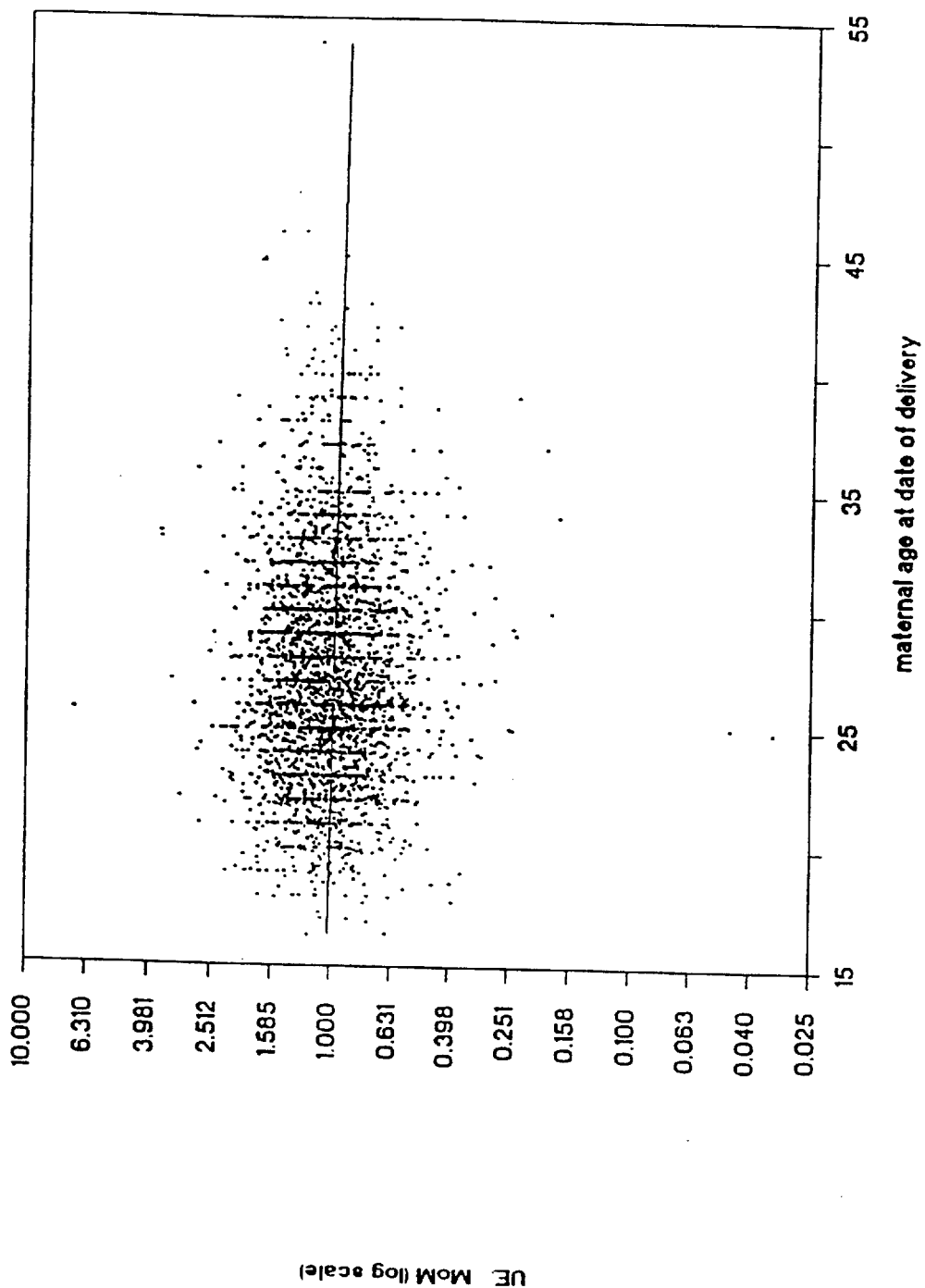
FIG. 7 is a plot of UE MoM (log scale) against maternal age at date of delivery for data from Trials B in Example 1.
Figure 8:
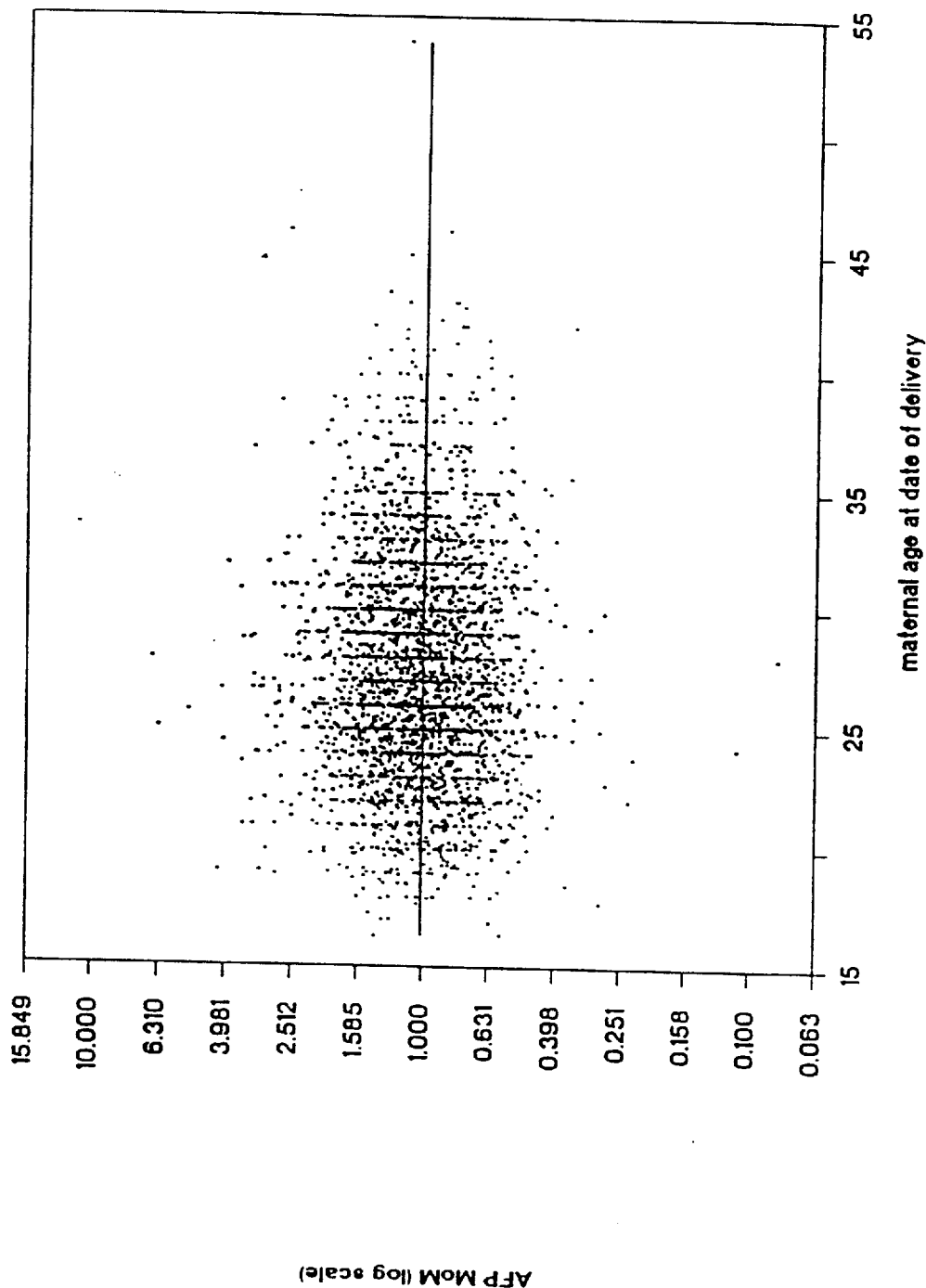
FIG. 8 is a plot of AFP MoM (log scale) against maternal age at date of delivery for data from Trials B in Example 1.
Figure 9:
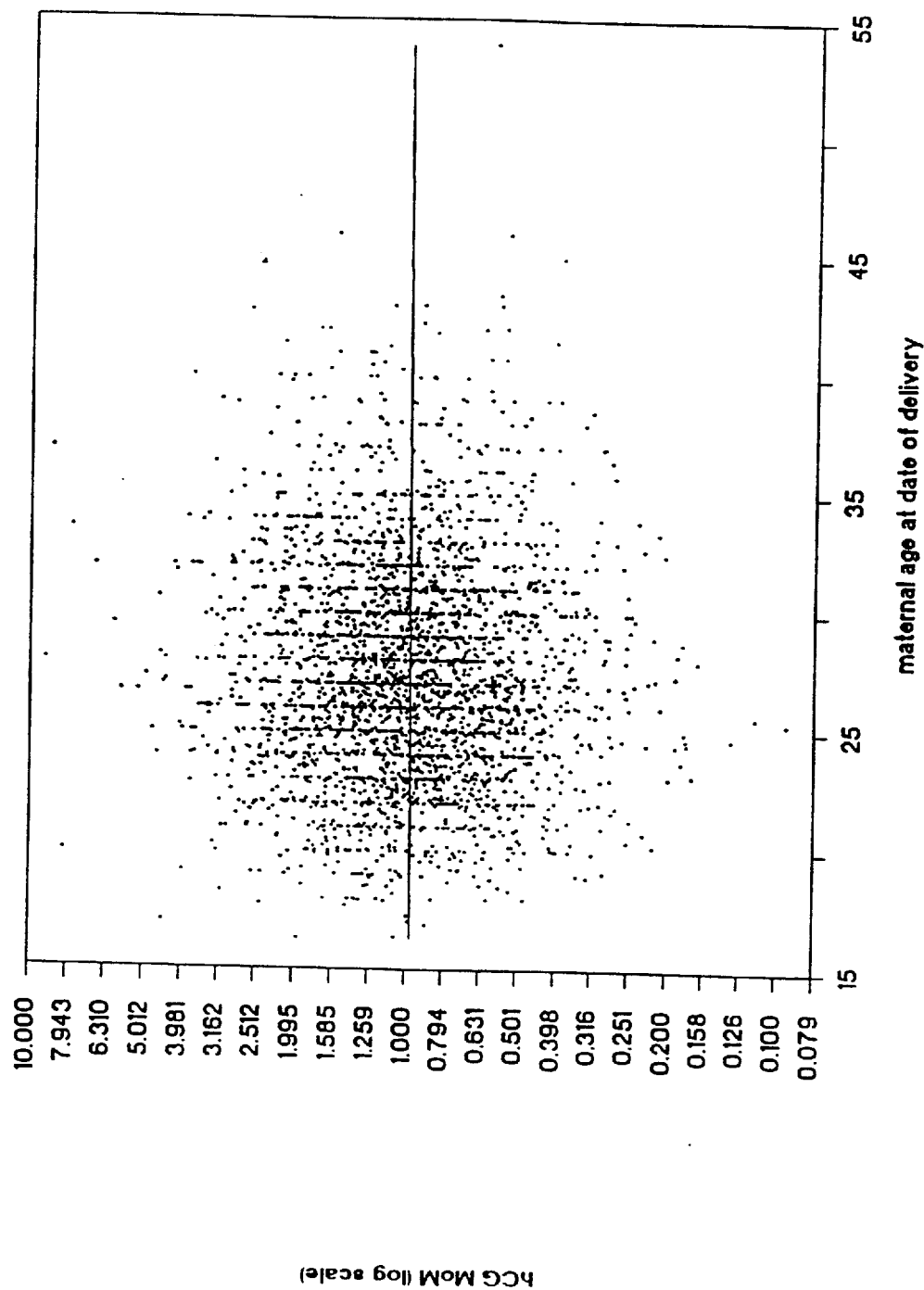
FIG. 9 is a plot of hCG MoM (log scale) against maternal age at date of delivery for data from Trials B in Example 1.

Examination of data from Trials B showed a strikingly similar effect, shown in FIG. 7. Again no relationship was found between maternal serum AFP MoM or hCG MoM and maternal age as shown in FIGS. 8 or 9 respectively.

Figure 10:
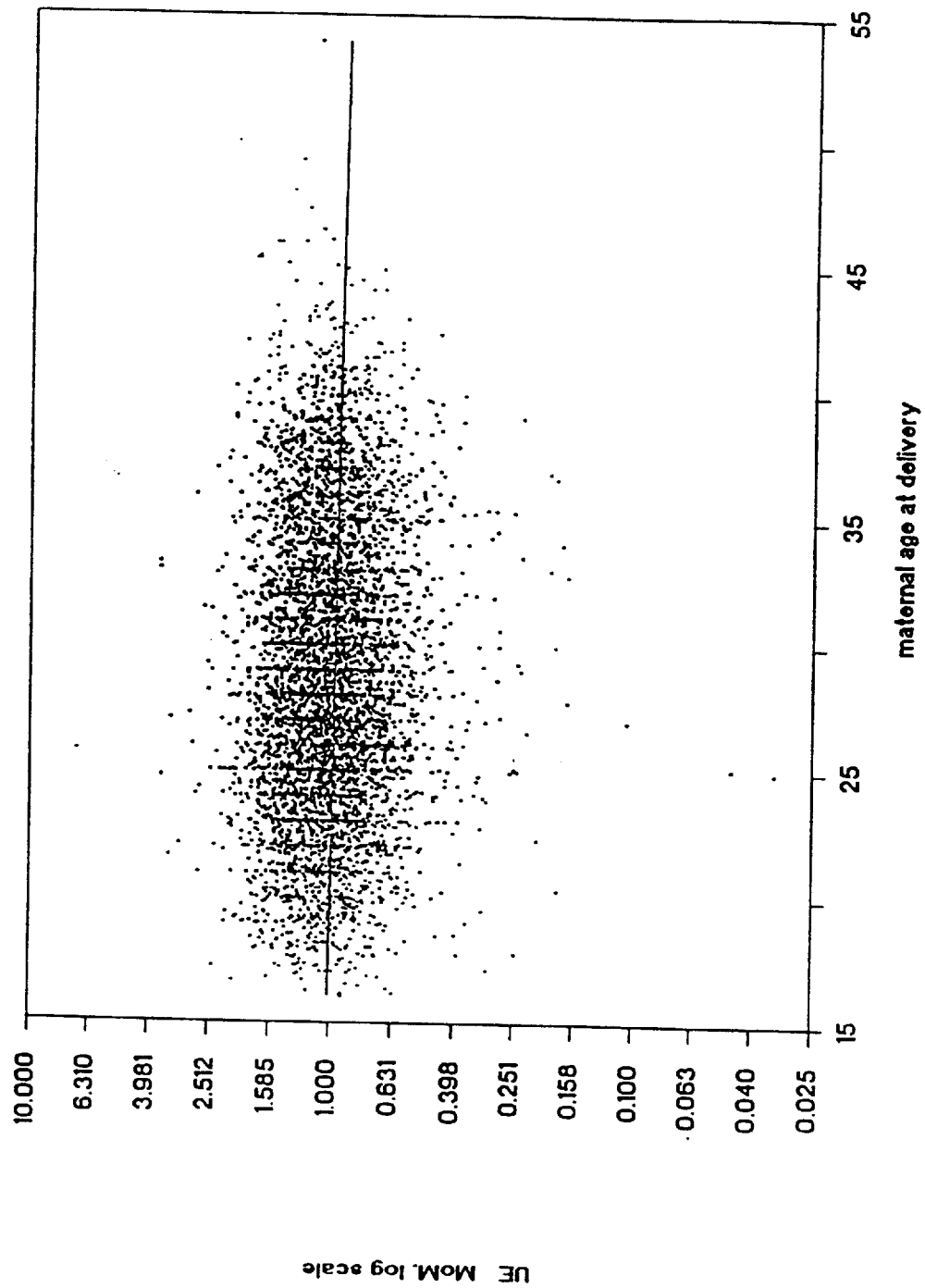
FIG. 10 is a plot of UE MoM (log scale) against maternal age at date of delivery for combined data from Trials A and B in Example 1.
Figure 11:
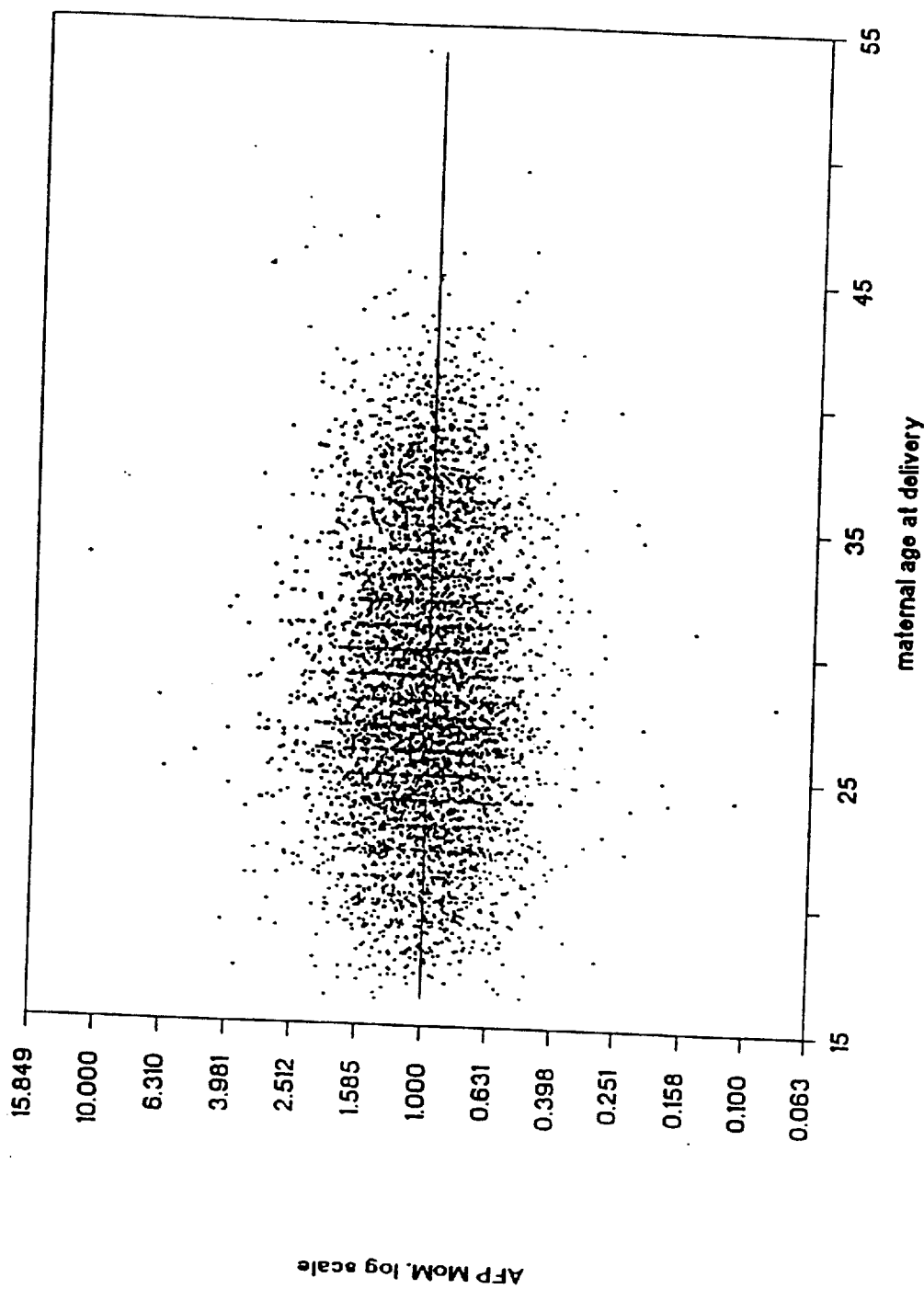
FIG. 11 is a plot of AFP MoM (log scale) against maternal age at date of delivery for combined data from Trials A and B in Example 1.
Figure 12:
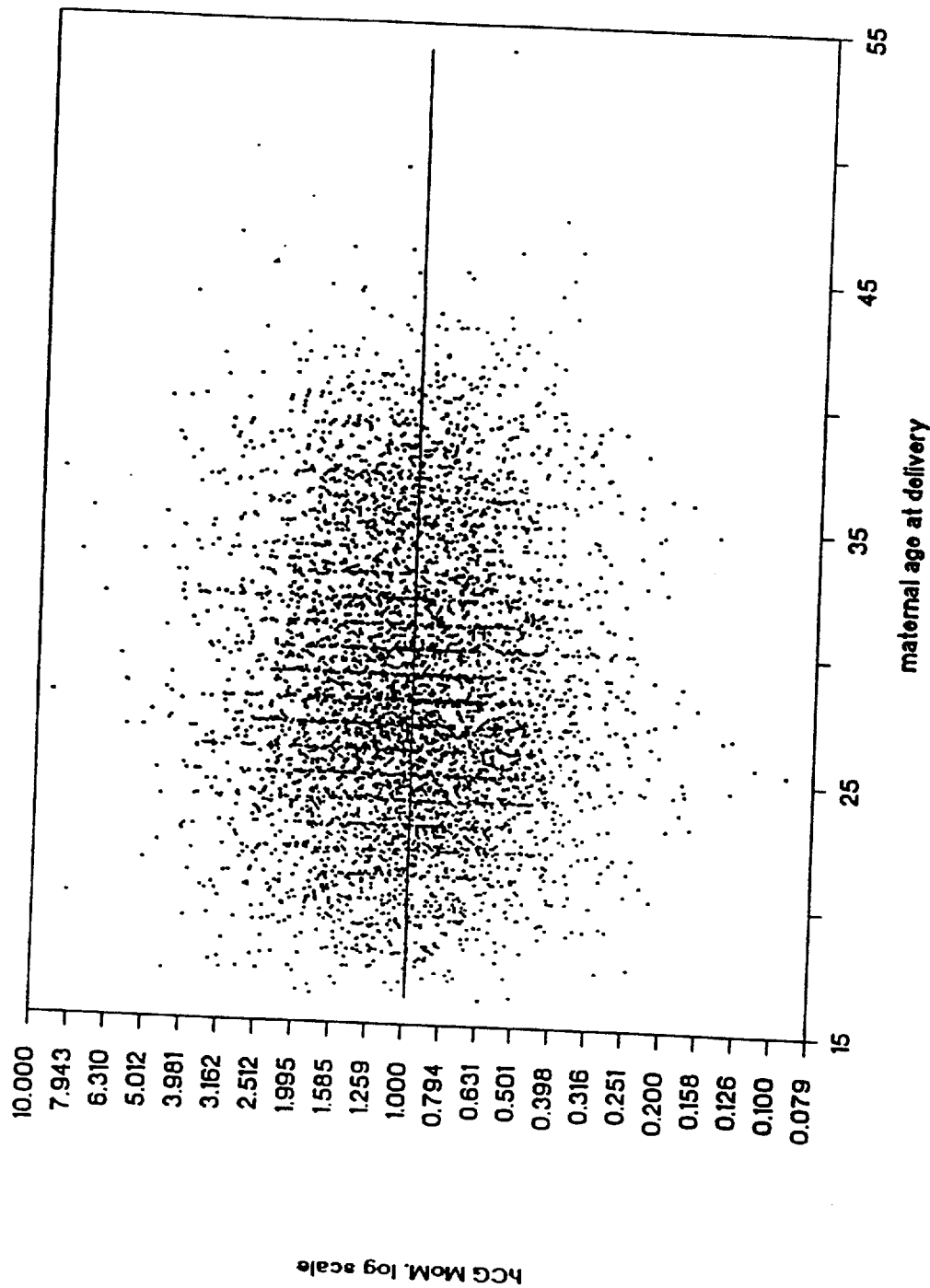
FIG. 12 is a plot of hCG MoM (log scale) against maternal age at date of delivery for combined data from Trials A and B in Example 1.

The relationship between maternal serum at the expected date of delivery and unconjugated estriol MoM for the combined data from Trials A and B is shown in FIG. 10. The combined data for maternal serum AFP MoM is shown in FIG. 11, and that for maternal serum hCG MoM in FIG. 12.

Table 1 shows the correlation and regression between unconjugated estriol and maternal age at the expected date of delivery (EDD) for Trials A and B, and for both trials combined.

TABLE 1

Regression of: log (UE MoM) = A * maternal age at EDD + B

|  | Trials A | Trials B | combined |
|---|---|---|---|
| Constant B | 0.0536 | 0.0616 | 0.0553 |
| Std Err of Constant B | 0.3344 | 0.3448 | 0.3401 |
| 95% CI of constant B |  |  |  |
| from | −0.6017 | −0.6141 | −0.6113 |
| to | 0.7090 | 0.7373 | 0.7218 |
| R Squared | 0.0022 | 0.0014 | 0.0018 |
| R value | 0.0470 | 0.0372 | 0.0420 |
| P value | p < 0.01 | p < 0.05 | p < 0.01 |
| No of Observations | 2545 | 3124 | 5669 |
| Degrees of Freedom | 2543 | 3122 | 5667 |
| A Coefficients | −0.0025 | −0.0028 | −0.0026 |
| Std Err of A Coefficient | 0.0010 | 0.0014 | 0.0008 |
| 95% CI of A coefficient |  |  |  |
| from | −0.0045 | −0.0055 | −0.0042 |
| to | −0.0004 | −0.0002 | −0.0010 |

Table 2 shows the lack of any statistically significant relationship between maternal serum AFP MoM and maternal age, and Table 3 similarly for maternal serum hCG and maternal age.

TABLE 2

Regression of: log (AFP MoM) = A * maternal age at EDD + B

|  | Trials A | Trials B | combined |
|---|---|---|---|
| Constant B | −0.0274 | 0.0172 | −0.0017 |
| Std Err of Constant B | 0.3715 | 0.3873 | 0.3803 |
| 95% CI of constant B |  |  |  |
| from | −0.7557 | −0.7420 | −0.7471 |
| to | 0.7008 | 0.7763 | 0.7436 |
| R Squared | 0.0002 | 0.0000 | 0.0008 |
| R value | 0.0130 | 0.0050 | 0.0050 |
| P value | n.s. | n.s. | n.s. |
| No of Observations | 2545 | 3124 | 5669 |
| Degrees of Freedom | 2543 | 3122 | 5667 |
| A Coefficients | 0.0008 | −0.0004 | 0.0001 |
| Std Err of A Coefficient | 0.0012 | 0.0015 | 0.0009 |
| 95% CI of A coefficient |  |  |  |
| from | −0.0015 | −0.0034 | −0.0017 |
| to | 0.0030 | 0.0026 | 0.0019 |

TABLE 3

Regression of: log (hCG MoM) = A * maternal age at EDD + B

|  | Trials A | Trials B | combined |
|---|---|---|---|
| Constant B | 0.0101 | −0.0451 | −0.0260 |
| Std Err of Constant B | 0.5407 | 0.5549 | 0.5486 |
| 95% CI of constant B |  |  |  |
| from | −1.0496 | −1.1327 | −1.1011 |
| to | 1.0698 | 1.0425 | 1.0492 |
| R Squared | 0.0000 | 0.0001 | 0.0000 |
| R value | 0.0034 | 0.0079 | 0.0058 |
| P value | n.s. | n.s. | n.s. |
| No of Observations | 2545 | 3124 | 5669 |
| Degrees of Freedom | 2543 | 3122 | 5667 |
| A Coefficients | −0.0003 | 0.0010 | 0.0006 |
| Std Err of A Coefficient | 0.0017 | 0.0022 | 0.0013 |
| 95% CI of A coefficient |  |  |  |
| from | −0.0036 | −0.0033 | −0.0020 |
| to | 0.0030 | 0.0053 | 0.0032 |

EXAMPLE 2

Formula for Adjusting UE MoM for Maternal Age

From the combined data from trials A and B it can be seen that the corrected normal UE median MoM can be obtained by the following relationship:

corrected normal median MoM =exp (−0.025758 * age at EDD+0.55278)

The corrected MoM for an individual woman is then calculated as follows:

Corrected MoM=Uncorrected MoM/Corrected normal median MoM

Table 4 shows the corrected MoM values for various combinations of maternal age at expected date of delivery and UE MoM values.

TABLE 4

|  | uncorrected UE MoM | | |
|---|---|---|---|
|  | 0.50 | 1.00 | 1.50 |
| Maternal age at EDD | corrected UE MoM | | |
| 15 | 0.4917 | 0.9835 | 1.4752 |
| 20 | 0.4981 | 0.9962 | 1.4944 |
| 30 | 0.5111 | 1.0222 | 1.5334 |
| 40 | 0.5245 | 1.0489 | 1.5734 |
| 45 | 0.5313 | 1.0625 | 1.5938 |

Using the statistical distributions of maternal serum UE in unaffected Down Syndrome affected pregnancies given by Wald et al for pregnancies dated by ultrasound (Wald et al, *British Journal of Obstetrics and Gynecology* 99, 144–149, 1992) it is possible to calculate the effects that such corrections would have on the risks assigned to an individual woman if she were to be screened for Down Syndrome using as an example a combination of her age and maternal serum unconjugated estriol.

Table 5 shows the individual risks which would be assigned to women of different ages with and without such correction for the effect of maternal age on unconjugated estriol levels.

TABLE 5

| age at EDD | age risk | uncorrected UE MoM | risk assessment uncorrected | corrected |
|---|---|---|---|---|
| 15 | 1:1578 | 0.40 | 1:21 | 1:24 |
| 15 | 1:1578 | 1.00 | 1:3134 | 1:3246 |
| 30 | 1:909 | 0.50 | 1:17 | 1:14 |
| 30 | 1:909 | 1.00 | 1:1877 | 1:1870 |
| 45 | 1:28 | 0.40 | 1:1 | 2:1 |
| 45 | 1:28 | 1.00 | 1:64 | 1.58 |

Correction for the influence of maternal age on unconjugated estriol levels has a direct influence on the assigned risk for fetal Down Syndrome. A typical risk cut-off would be set at a risk of 1:250 as this approximately equals the risk of losing the baby through miscarriage as a result of the diagnostic amniocentesis. Depending upon the unconjugated estriol level and the mother's age the change could be sufficient for their risk to be altered from what would be considered high risk to low risk and vice-versa. Some typical examples of these changes are shown in Table 6.

TABLE 6

| age at EDD | age risk | uncorrected UE MoM | Risk Assessment Uncorrected | Corrected |
|---|---|---|---|---|
| 30 | 1:909 | 0.58 | 1:239 | 1:256 |
| 35 | 1:384 | 0.70 | 1:281 | 1:241 |
| 40 | 1:112 | 1.00 | 1:252 | 1:230 |

A second consequence of such a correlation is that it would be expected to lead to a slight reduction in the overall variance of UE MoM, and a consequential decrease in the numbers of women who screen-positive with such a test.

The changes illustrated have occurred when using maternal age and unconjugated estriol as a screening test. The changes in risk-assessment as a consequence of the relationship between maternal age and unconjugated estriol will still be present even if further analytes are added to the risk assessment, such as AFP, hCG, the free beta or free alpha subunit of hCG, or any other maternal serum or fetal biometric marker for fetal abnormality.

Unconjugated estriol is also known to be a marker for Trisomy 18 and for anencephaly and similar arguments apply for the inclusion of a maternal age correction factor to the UE MoM when screening for those conditions.

The invention has been described in detail with particular reference to preferred embodiments thereof, but it will be understood that variations and modifications can be effected within the spirit and scope of the invention.

I claim:

1. An apparatus comprising:
  a means adapted for receiving measurements of a pregnant woman's maternal blood concentration of unconjugated estriol its precursors, its metabolites, or a mixture thereof, and
  a computer programmed to carry out the following activities:
  A) determining a pregnant patient's prior risk of carrying a fetus having said chromosomal abnormality,
  B) calculating a normalized value of said concentration of unconjugated estriol its precursors, its metabolites, or a mixture thereof, by dividing by a median value found in a population of women with unaffected pregnancies with the same gestational age as said pregnant patient,
  C) correcting said normalized value for influence of maternal age by dividing said normalized value by a corrected normal median value for a population of women of that maternal age,
  D) calculating a first probability that the corrected normalized value is part of a Gaussian distribution of values found in pregnancies with said chromosomal abnormality,
  E) calculating a second probability that the corrected normalized value is a part of a Gaussian distribution of values found in unaffected pregnancies,
  F) calculating a likelihood ratio, said likelihood ratio being the ratio of said first probability and said second probability, and
  G) modifying said prior risk by the likelihood ratio.

2. A method for antenatal risk assessment for a chromosomal abnormality in a fetus, comprising:
  A) calculating a pregnant patient's prior risk of carrying a fetus having said chromosomal abnormality,
  B) measuring said pregnant patient's blood for a concentration of unconjugated estriol, its precursors, its metabolites, or a mixture thereof,
  C) calculating a normalized value of said concentration by dividing by a median value found in a population of women with unaffected pregnancies with the same gestational age as said pregnant patient,
  D) correcting said normalized value for influence of maternal age by dividing said normalized value by a corrected normal median value for a population of women of that maternal age,
  E) calculating a first probability that the corrected normalized value is part of a Gaussian distribution of values found in pregnancies with said chromosomal abnormality,
  F) calculating a second probability that the corrected normalized value is a part of a Gaussian distribution of values found in unaffected pregnancies,
  G) calculating a likelihood ratio, said likelihood ratio being the ratio of said first probability and said second probability, and
  H) modifying said prior risk by the likelihood ratio.

3. The method according to claim 2, wherein said chromosomal abnormality is selected from the group consisting of Down Syndrome, Trisomy 18, Trisomy 13, and Turner Syndrome.

* * * * *